(12) United States Patent
Balthasart et al.

(10) Patent No.: US 8,071,827 B2
(45) Date of Patent: *Dec. 6, 2011

(54) PROCESS FOR THE MANUFACTURE OF 1,2-DICHLOROETHANE

(75) Inventors: Dominique Balthasart, Brussels (BE); Michel Strebelle, Brussels (BE)

(73) Assignee: Solvay (Societé Anonyme), Brussels (BE)

( * ) Notice: Subject to any disclaimer, the term of this patent is extended or adjusted under 35 U.S.C. 154(b) by 280 days.

This patent is subject to a terminal disclaimer.

(21) Appl. No.: 12/304,379

(22) PCT Filed: Jun. 22, 2007

(86) PCT No.: PCT/EP2007/056264
§ 371 (c)(1),
(2), (4) Date: Dec. 11, 2008

(87) PCT Pub. No.: WO2008/000702
PCT Pub. Date: Jan. 3, 2008

(65) Prior Publication Data
US 2009/0270579 A1    Oct. 29, 2009

(30) Foreign Application Priority Data
Jun. 26, 2006 (FR) .................... 06 05717

(51) Int. Cl.
C07C 17/15 (2006.01)
C07C 17/10 (2006.01)
(52) U.S. Cl. .................. 570/223; 570/224; 570/230
(58) Field of Classification Search ........... 570/223, 570/224, 230
See application file for complete search history.

(56) References Cited

U.S. PATENT DOCUMENTS

| | | | |
|---|---|---|---|
| 4,910,354 A | 3/1990 | Derleth et al. |
| 5,260,247 A | 11/1993 | Helmut et al. |
| 5,527,754 A | 6/1996 | Derleth et al. |
| 6,803,342 B1 | 10/2004 | Derleth et al. |
| 7,667,084 B2 | 2/2010 | Strebelle et al. |
| 2004/0267063 A1 | 12/2004 | Harth et al. |
| 2008/0108856 A1 | 5/2008 | Strebelle et al. |
| 2008/0207966 A1 | 8/2008 | Balthasart et al. |
| 2008/0207967 A1 | 8/2008 | Strebelle et al. |
| 2008/0207968 A1 | 8/2008 | Strebelle et al. |
| 2009/0203854 A1 | 8/2009 | Strebelle et al. |
| 2009/0270568 A1 | 10/2009 | Strebelle et al. |
| 2009/0326179 A1 | 12/2009 | Balthasart et al. |

FOREIGN PATENT DOCUMENTS

| | | |
|---|---|---|
| EP | 0255156 A1 | 2/1988 |
| EP | 0494474 A1 | 7/1992 |
| EP | 0657212 A1 | 6/1995 |
| EP | 0657213 A1 | 6/1995 |
| NL | 6901398 | 11/1969 |
| WO | WO0026164 A1 | 5/2000 |
| WO | WO03048088 A1 | 6/2003 |
| WO | WO2006/067188 A1 | 6/2006 |
| WO | WO2006/067190 A1 | 6/2006 |
| WO | WO2006/067191 A1 | 6/2006 |
| WO | WO2006/067192 A1 | 6/2006 |
| WO | WO2007/147870 A1 | 12/2007 |
| WO | WO2008/000693 A1 | 1/2008 |
| WO | WO2008/000705 A1 | 1/2008 |
| WO | WO2008/107468 A1 | 9/2008 |
| WO | WO2009/106479 A1 | 9/2009 |
| WO | WO2009/147076 A1 | 12/2009 |
| WO | WO2009/147083 A1 | 12/2009 |
| WO | WO2009/147100 A1 | 12/2009 |
| WO | WO2009/147101 A1 | 12/2009 |

OTHER PUBLICATIONS

PCT International Search Report dated Aug. 30, 2007 for International Application No. PCT/EP2007/056264 (2 p.).
U.S. Appl. No. 12/919,101, filed Aug. 24, 2010, Petitjean et al.
U.S. Appl. No. 12/995,486, filed Dec. 1, 2010, Lempereur et al.
U.S. Appl. No. 12/995,518, filed Dec. 1, 2010, Petitjean et al.
U.S. Appl. No. 12/995,539, filed Dec. 1, 2010, Lempereur et al.
U.S. Appl. No. 12/995,509, filed Dec. 1, 2010, Kotter et al.

*Primary Examiner* — Jafar Parsa
(74) *Attorney, Agent, or Firm* — Beatrice C. Ortego

(57) ABSTRACT

Process for the manufacture of 1,2-dichloroethane (DCE) starting from a stream of ethane which is subjected to a catalytic oxydehydrogenation (ODH) producing a gas mixture containing ethylene, then dried and subjected to an absorption to be separated into a fraction enriched with the compounds that are lighter than ethylene containing some of the ethylene conveyed to a chlorination reactor in which most of the ethylene is converted to DCE, and into a fraction F1. Fraction F1 is then subjected to a desorption to be separated into a fraction enriched with ethylene conveyed to an oxychlorination reactor in which most of the ethylene is converted into DCE, and into a fraction F3.

25 Claims, 2 Drawing Sheets

PROCESS FOR THE MANUFACTURE OF 1,2-DICHLOROETHANE

CROSS-REFERENCE TO RELATED APPLICATIONS

The present application is a U.S. national stage application under 35 U.S.C. §371 of International Application No. PCT/EP2007/056264, filed Jun. 22, 2007, which claims benefit of French patent applications FR 06.05717 filed on Jun. 26, 2006, all of these applications being herein incorporated by reference in their entirety for all purposes.

TECHNICAL FIELD OF THE INVENTION

The present invention relates to a process for the manufacture of 1,2-dichloroethane (DCE), a process for the manufacture of vinyl chloride (VC) and a process for the manufacture of polyvinyl chloride (PVC).

BACKGROUND OF THE INVENTION

DCE is usually prepared by oxychlorination of ethylene using hydrogen chloride (HCl) and a source of oxygen or by direct chlorination of ethylene using chlorine. The dehydrochlorination of DCE by pyrolysis thus results in the production of VC with release of HCl. The oxychlorination and chlorination are generally carried out in parallel and the HCl produced in the pyrolysis is used in the oxychlorination.

To date, ethylene which is more than 99.8% pure is normally used for the manufacture of DCE. This very high purity ethylene is obtained via the thermal cracking of various petroleum products, followed by numerous complex and expensive separation operations in order to isolate the ethylene from the other products of the cracking and to obtain a product of very high purity.

Given the high cost linked to the production of ethylene of such high purity, and also the advantage that there could be in envisaging a process for the manufacture of VC by DCE in favourable regions that lack accessible ethylene capacities, various processes for the manufacture of DCE using ethylene having a purity of less than 99.8% have been envisaged. These processes have the advantage of reducing the costs by simplifying the course of separating the products resulting from cracking of petroleum products and by thus abandoning complex separations which are of no benefit for the manufacture of DCE.

Thus, various processes for the manufacture of DCE starting from ethylene having a purity of less than 99.8% produced by simplified cracking of ethane have been envisaged.

For example, Patent Application WO 00/26164 describes a process for the manufacture of DCE by chlorination of ethylene obtained by simplified cracking of ethane, the chlorination taking place in the presence of impurities obtained during the cracking of ethane without any other purification.

Patent Application WO 03/48088 itself describes a process for the manufacture of DCE by dehydrogenation of ethane giving rise to the formation of a fraction comprising ethane, ethylene and impurities including hydrogen, which fraction is then subjected to a chlorination and/or oxychlorination.

These processes have the disadvantage that the ethylene obtained cannot be used for a combined ethylene chlorination/oxychlorination process given that the ethylene contains impurities whose presence during the oxychlorination reaction could cause operating problems, namely poisoning of the catalyst by the heavy products and an uneconomic conversion of the hydrogen present. This hydrogen conversion would consume high-purity oxygen which would thus be sacrificed for an undesired reaction and would release a high heat of reaction during the conversion of hydrogen to water. This conversion would then limit the capability of the oxychlorination reactor, generally linked to the heat exchange capability. An unusually high investment must therefore be expended in order to guarantee the heat exchange area, and thereby the reactor volume, caused by the presence of hydrogen in the mixture.

The option taken of burning the hydrogen in a separate reactor, described in Application WO 03/48088, does not resolve the difficulty because it requires a large amount of oxygen, a stoichiometric amount relative to hydrogen, and also a large surface area for exchange to eliminate this heat of combustion. Consequently it has a significant ethylene consumption and it may have problems linked to safety. Finally, the removal of the water formed leads to an increase in the production costs.

Processes in which VC is obtained by oxychlorination of ethane and not of ethylene are also known. Such processes have not found an industrial application up till now given that as they are conducted at high temperatures, they result in a mediocre selectivity with loss of the reactants used and costs for separating and destroying the by-products and they are also characterized by problems of behaviour of the material in a corrosive oxychlorination medium. Finally, problems linked to the behaviour of the catalysts used owing to the gradual vaporization of their constituents and also linked to the deposition of these constituents on the cold surface of the exchanger bundle are usually encountered.

SUMMARY OF THE INVENTION

One object of the present invention itself is to provide a process using ethylene having a purity of less than 99.8% which has the advantage of reducing the costs linked to the production of ethylene of higher purity and which has the advantage of avoiding the abovementioned problems.

To this effect, the invention relates to a process for the manufacture of DCE starting from a stream of ethane according to which:

a) the stream of ethane is subjected to a catalytic oxydehydrogenation producing a gas mixture containing ethylene, unconverted ethane, water and secondary constituents;

b) said gas mixture is optionally washed and dried thus producing a dry gas mixture;

c) after an optional additional purification step, said dry gas mixture is subjected to an absorption A1 which consists of separating said gas mixture into a fraction enriched with the compounds that are lighter than ethylene containing some of the ethylene (fraction A) and into a fraction F1;

d) fraction A is conveyed to a chlorination reactor in which most of the ethylene present in fraction A is converted to 1,2-dichloroethane and optionally the 1,2-dichloroethane obtained is separated from the stream of products derived from the chlorination reactor;

e) optionally the stream of products derived from the chlorination reactor, from which the 1,2-dichloroethane has optionally been extracted, is subjected to an absorption A2 which consists of separating said stream into a fraction enriched with ethane F2 which is then conveyed back to fraction F1, and into a fraction enriched with compounds that are lighter than ethane F2';

f) fraction F1, optionally containing fraction F2 recovered in step e) of absorption A2, is subjected to a desorption D which consists of separating fraction F1 into a fraction enriched with ethylene (fraction B) and into a fraction F3, optionally containing the 1,2-dichloroethane formed in the chlorination reactor then extracted if it has not been extracted previously, which is recycled to at least one of the absorption steps, optionally after an additional treatment intended to reduce the concentration of compounds that are heavier than ethane in fraction F3;

g) fraction B is conveyed to an oxychlorination reactor in which most of the ethylene present in fraction B is converted into 1,2-dichloroethane, the 1,2-dichloroethane obtained is separated from the stream of products derived from the oxychlorination reactor and is optionally added to the 1,2-dichloroethane formed in the chlorination reactor; and the stream of products derived from the oxychlorination reactor, from which the 1,2-dichloroethane has been extracted, optionally containing an additional stream of ethane previously introduced in one of steps b) to g), is optionally recycled to step a) after having been optionally purged of gases and/or after an optional additional treatment in order to eliminate the chlorinated products contained therein.

BRIEF DESCRIPTION OF THE DRAWINGS

For a detailed description of the invention, reference will now be made to the accompanying drawings in which.

DETAILED DESCRIPTION OF PREFERRED EMBODIMENTS

Figure 1:
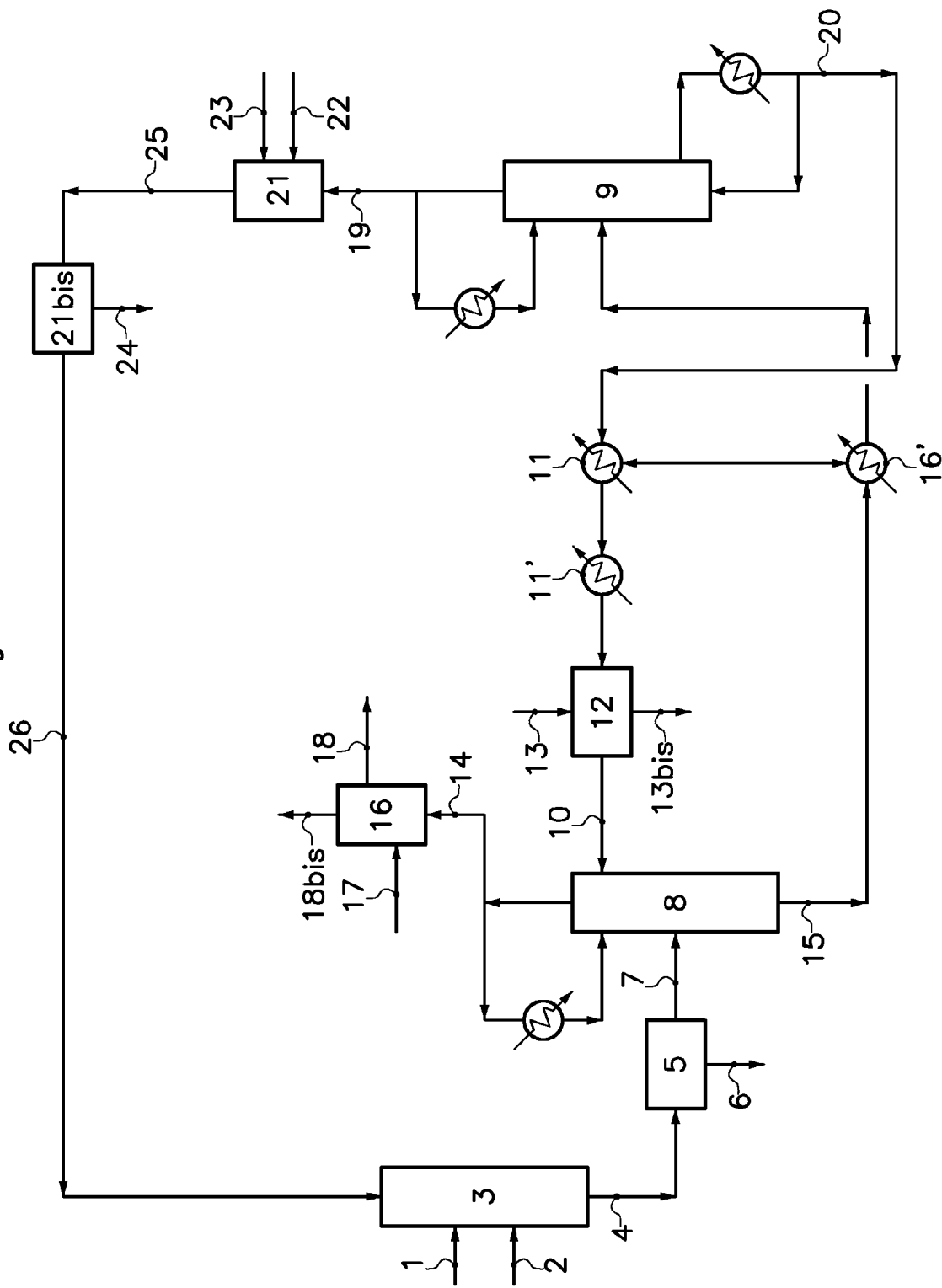
FIG. 1 illustrates a first preferred mode of the process for the manufacture of DCE according to the invention.

According to step a) of the process according to the invention, the stream of ethane is subjected to a catalytic oxydehydrogenation producing a gas mixture containing ethylene, unconverted ethane, water and secondary constituents.

The stream of ethane subjected to the catalytic oxydehydrogenation may or may not be chemically pure. The stream of ethane used may contain up to 70 vol % of other gases such as methane, hydrogen, ethylene, oxygen, nitrogen and carbon oxides.

The stream of ethane used advantageously contains at least 80 vol %, preferably at least 90 vol %, particularly preferably at least 95 vol % and more particularly preferably at least 98 vol % of ethane. If necessary, the ethane may be separated from the secondary compounds having a higher boiling point in any known device, for example by absorption, extraction, diffusion or distillation.

The stream of ethane subjected to the catalytic oxydehydrogenation may be a source of ethane such as is available on the market but also the stream of products derived from the oxychlorination reactor, from which the 1,2-dichloro-ethane has been extracted, optionally containing an additional stream of ethane added to one of steps b) to g) and recycled to step h), or a mixture of the two.

The term "catalytic oxydehydrogenation (ODH)", also known as catalytic oxidative dehydrogenation, is understood to mean a partial oxidation of ethane by oxygen in the presence of a catalyst.

ODH may take place either at a temperature above 650° C. up to 800° C., below the range of thermal cracking temperatures, or at a temperature less than or equal to 650° C.

The pressure at which step a) is carried out is advantageously at least 1, preferably at least 1.5 and particularly preferably at least 2 bar absolute. It is advantageously at most 16, preferably at most 11 and particularly preferably at most 6 bar absolute.

The oxygen introduced may be oxygen or a gas containing oxygen with other inert gases, such as for example air. Preferably, oxygen is used. The oxygen may or may not be chemically pure. Thus, it is possible to use a very pure source of oxygen containing at least 99 vol % of oxygen but also a source of oxygen containing less than 99 vol % of oxygen. In the latter case, the oxygen used advantageously contains more than 90 vol % and preferably more than 95 vol % of oxygen. A source of oxygen containing from 95 to 99 vol % of oxygen is particularly preferred.

The amount of oxygen introduced, based on the amount of ethane, is advantageously from 0.001 to 1 mol/mol, preferably from 0.005 to 0.5 mol/mol and particularly preferably from 0.05 to 0.3 mol/mol.

ODH may be carried out in any known device. Advantageously, ODH is carried out in one reactor or a series of reactors of fixed bed type having one or more beds, between which a thermal conditioning step may be carried out, or in one reactor or a series of reactors of fluid bed type, preferably adiabatic or with temperature control using an auxiliary fluid inside the reactor (multitubular reactor or heat exchanger immersed in the catalytic bed) or outside the reactor. The reactants may be previously mixed before introduction into the reaction zone. One or more reactants may also be added differently, for example between the beds of a multi-bed reactor. The reactor may be equipped with preheating means and with any means necessary to control the reaction temperature. A cross exchanger advantageously enables the heat of the products formed to be recovered to reheat the incoming products.

Various catalytic systems may be used to carry out ODH according to the invention.

Thus, mention may be made of catalysts based on alkaline-earth oxides, such as for example Li/MgO catalysts generally operating at temperatures above 600° C. Mention may also be made of catalysts based on nickel (Ni). Catalysts containing molybdenum (Mo) and/or vanadium (V) have a particular advantage. These catalysts are generally based on oxides of these elements. They advantageously contain, in addition, other elements such as, for example Cr, Mn, Nb, Ta, Te, Ti, P, Sb, Bi, Zr, Ni, Ce, Al, Ca or W.

Catalysts based vanadium (V) are more particularly advantageous.

Mixed oxides containing V and at least one other element chosen from Mo, W, Nb, Ta, Te, Ti, P, Sb, Bi, Zr, Ni, Ce, Al and Ca are preferred.

Mixed oxides containing both Mo and V, W and V or Mo, W and V are particularly preferred.

Among those containing Mo and V, mention may be made of Mo—V—O, Mo—V—Zr—O, Mo—V—Ta—Sb—Zr—O, Mo—V—Ta—Sb—O, Mo—V—Nb—Te—O, Mo—V—Nb—Bi—Ni—O, Mo—V—Nb—Bi—O, Mo—V—Nb—Ni—O, Mo—V—Nb—Sb—Ca—O, Mo—V—Ta—Al—O, Mo—V—Ta—O, Mo—V—Al—O, Mo—V—Sb—O, Mo—V—Nb—O and Mo—V—Nb—Sb.

Among those containing W and V, mention may be made of W—V—O, W—V—Nb—O, and W—V—Ta—O.

Among those containing Mo, W and V, mention may be made of Mo—W—V—Ta—Te—Ti—P—Ni—Ce—O, Mo—W—V—Ta—Te—Ti—P—O, Mo—W—V—Te—Ti—P—Ce—O, Mo—W—V—Te—Ti—P—Ni—O, Mo—W—V—Te—Ti—P—O, Mo—W—V—Te—Ti—O, Mo—W—V—Te—P—O, Mo—W—V—Te—O, Mo—W—V—Ta—Te—Ti—P—Ni—Ce—O, Mo—W—

V—Ta—Te—Ti—P—O, Mo—W—V—Te—Ti—P—Ce—O, Mo—W—V—Te—Ti—P—Ni—O, Mo—W—V—Te—Ti—P—O, Mo—W—V—Te—Ti—O, Mo—W—V—Te—P—O, Mo—W—V—Te—O, Mo—W—V—Nb—O, Mo—W—V—Sb—O, Mo—W—V—Ti—Sb—Bi—O, Mo—W—V—Ti—Sb—O, Mo—W—V—Sb—Bi—O, Mo—W—V—Zr—O, Mo—W—V—Nb—Ta—O, Mo—W—V—Nb—O and Mo—W—V—O.

Ta—Ni—O, Nb—Ni—O and Nb—Ta—Ni—O catalysts could also be used.

The catalysts used for ODH may or may not be supported. In the case where they are supported, the support which may possibly be used includes silica, alumina, titanium oxide, silicon carbide, zirconia and mixtures thereof such as mixed oxides.

The catalysts used for ODH are advantageously resistant to DCE. The catalyst used may be placed on a bed or in tubes or outside of those tubes so that a temperature control may be obtained by a fluid surrounding these tubes or running through them.

ODH of the stream of ethane gives a gas mixture containing ethylene, unconverted ethane, water and secondary constituents. The secondary constituents may be carbon monoxide, carbon dioxide, hydrogen, various oxygen-containing compounds such as, for example, acetic acid or aldehydes, nitrogen, methane, oxygen, optionally acetylene and optionally organic compounds comprising at least 3 carbon atoms.

According to a first variant of the process according to the invention, ODH takes place at a temperature above 650° C. up to 800° C.

According to a second variant of the process according to the invention, ODH takes place at a temperature less than or equal to 650° C.

Advantageously, ODH then takes place at a temperature less than or equal to 600° C., preferably less than or equal to 550° C., particularly preferably less than or equal to 500° C., more particularly preferably less than or equal to 450° C. and most particularly preferably less than or equal to 400° C. A temperature between 200 and 400° C. is particularly advantageous.

In this case, the process according to the invention has the advantage of generating very small amounts of hydrogen responsible for many drawbacks.

According to this second variant, advantageously ODH makes it impossible to generate heavy compounds having a number of carbon atoms greater than or equal to 3, such as for example propylene and olefins whose molecular weight is higher than that of propylene, in troublesome amounts.

The second variant of the process according to the invention is preferred to the first.

According to step b) of the process according to the invention, said gas mixture obtained in step a) is optionally washed and it is dried thus producing a dry gas mixture.

The gas mixture obtained in step a) may or may not be washed. Preferably, it is washed. Washing of the gas mixture obtained in step a) may be carried out by any known means. Preferably, it is carried out using an aqueous, preferably alkaline, washing liquid, or using a non-aqueous liquid. Among the aqueous washing liquids, mention may be made of sodium hydroxide, sodium carbonate, sodium hydrogencarbonate and sodium hydroxide. Among the non-aqueous liquids, mention may be made of methylpyrrolidone, heavy oils and methanol. By this operation, solids such as coal, sulfur compounds, carbon dioxide, saturated or unsaturated hydrocarbons that are heavier than ethylene, acetylene, acid species such as acetic acid or hydrogen chloride and aldehydes are advantageously removed.

Drying of the gas mixture may then be carried out by any known means. Preferably, drying is carried out by cooling at the end of a compression of the gases and/or by adsorption on a solid desiccant such as a molecular sieve, alumina or lime.

The washing step, when it takes place, and the drying step may take place in any order. Thus, it is possible to wash and then dry the gas mixture or to dry it and then wash it. Preferably, said gas mixture obtained in step a) is washed then it is dried, thus producing a dry gas mixture.

After step b), the amount of water in the dry gas mixture is advantageously less than or equal to 500 ppm, preferably less than or equal to 10 ppm and particularly preferably less than or equal to 1 ppm by volume.

An additional purification step, preferably a chemical purification step, of the dry gas mixture may be envisaged before it enters into the chlorination reactor in order to remove any compound that is not desired in the chlorination. This may be the case for acetylene, for example, formed during step a) but also for oxygen which is undesired when in excess.

The acetylene may advantageously be removed via a hydrogenation, preferably by means of the hydrogen present in the mixture.

This step must take place at the latest just before the chlorination step. It may take place between step b) and step c), during step c) or just before step d). Preferably, it takes place between step b) and step c).

After step b) defined above, and the optional additional purification step, said dry gas mixture is subjected to step c) of absorption A1 which consists of separating said gas mixture into a fraction enriched with the compounds that are lighter than ethylene containing some of the ethylene (fraction A) and into a fraction F1.

Thus, the dry gas mixture is subjected to an absorption step A1 in which said stream is preferably brought into contact with a washing agent containing DCE.

The expression "washing agent containing DCE" or more simply "washing agent" is understood to mean a composition in which the DCE is present in the liquid state.

The washing agent that can be used for the absorption step A1 therefore advantageously contains DCE in the liquid state. The presence, in said washing agent, of other compounds is not at all excluded from the scope of the invention. However, it is preferred that the washing agent contains at least 50 vol % of DCE, more particularly at least 80 vol % and most particularly preferably at least 95 vol %.

The washing agent used for the absorption step A1 may be composed of fresh washing agent of any origin, for example crude DCE exiting the chlorination unit, crude DCE exiting the oxychlorination unit or a mixture of the two which has not been purified. It may also be composed of said DCE that has been previously purified or all or part of fraction F3 recovered during the desorption step D of the process according to the invention optionally containing the DCE formed in the chlorination reactor and extracted in the desorption step, after an optional additional treatment making it possible to reduce the concentration, in fraction F3, of the compounds that are heavier than ethane, as explained below, optionally with the addition of fresh washing agent.

Preferably, the washing agent used for the absorption step A1 is composed of all or part of fraction F3 recovered during the desorption step D of the process according to the invention optionally containing the DCE formed in the chlorination reactor and extracted in the desorption step, after the above-mentioned optional treatment, optionally with the addition of fresh washing agent. In the case where the DCE formed in the chlorination reactor is isolated from the stream of products derived from the chlorination reactor at the chlorination outlet, in a particularly preferred manner, the washing agent used for the absorption step A1 is composed of all or part of fraction F3 recovered during the desorption step D of the process according to the invention, after the abovementioned optional treatment, with the addition of fresh washing agent (to compensate for losses of washing agent during the absorption and desorption steps).

The abovementioned optional additional treatment making it possible to reduce the concentration, in fraction F3, of the compounds that are heavier than ethane, preferably of the compounds comprising at least 3 carbon atoms, may be a step of desorbing the compounds that are heavier than ethane and lighter than fraction F3 or a step of distilling fraction F3. Preferably, it consists of desorbing the compounds that are heavier than ethane and lighter than fraction F3. Preferably, this treatment of fraction F3 takes place.

An essential advantage lies in the fact that the presence of this DCE is in no way troublesome, as it is the compound mainly formed during the oxychlorination or chlorination.

The ratio between the respective throughputs of washing agent and ethylene to be extracted from the dry gas mixture is not critical and can vary to a large extent. It is in practice only limited by the cost of regenerating the washing agent. In general, the throughput of washing agent is at least 1, preferably at least 5 and particularly preferably at least 10 tonnes per tonne of dry gas mixture. In general, the throughput of washing agent is at most 100, preferably at most 50 and particularly preferably at most 25 tonnes per tonne of ethylene and ethane to be extracted from the dry gas mixture.

The absorption step A1 is advantageously carried out using an absorber such as, for example, a climbing film or falling film absorber or an absorption column chosen from plate columns, columns with random packing, columns with structured packing, columns combining one or more of the aforementioned internals and spray columns. The absorption step A1 is preferably carried out using an absorption column and particularly preferably using a plate absorption column.

The absorption column is advantageously equipped with associated accessories such as, for example, at least one condenser or chiller that is internal or external to the column.

The abovementioned absorption step A1 is advantageously carried out at a pressure of at least 15, preferably of at least 20 and particularly preferably of at least 25 bar absolute. The absorption step A1 is advantageously carried out at a pressure of at most 40, preferably of at most 35 and particularly preferably of at most 30 bar absolute.

The temperature at which the absorption step A1 is carried out is advantageously at least −10, preferably at least 0 and particularly preferably at least 10° C. at the top of the absorber or absorption column. It is advantageously at most 60, preferably at most 50 and particularly preferably at most 40° C. at the top of the absorber or absorption column.

The temperature at the bottom of the absorber or absorption column is at least 0, preferably at least 10 and particularly preferably at least 20° C. It is advantageously at most 70, preferably at most 60 and particularly preferably at most 50° C.

Step c) of absorption A1 consists of separating said gas mixture into a fraction enriched with the compounds that are lighter than ethylene containing some of the ethylene (fraction A) and into a fraction F1.

Fraction A is enriched with the compounds that are lighter than ethylene. These compounds are generally methane, nitrogen, oxygen, hydrogen and carbon monoxide.

Advantageously, fraction A contains at least 70%, preferably at least 80% and particularly preferably at least 85% by weight of the compounds that are lighter than ethylene contained in the dry gas mixture. Advantageously, fraction A contains at most 99.99%, preferably at most 99.95% and particularly preferably at most 99.9% by weight of the compounds that are lighter than ethylene contained in the dry gas mixture.

Fraction A is characterized by an acetylene content that is advantageously less than or equal to 0.01%, preferably less than or equal to 0.005% and particularly preferably less than or equal to 0.001% by volume relative to the total volume of fraction A.

Advantageously, fraction A contains at most 20%, preferably at most 10% and particularly preferably at most 5% of ethane relative to the total volume of fraction A.

Fraction A is characterized by a content of compounds comprising at least 3 carbon atoms that is advantageously less than or equal to 0.01%, preferably less than or equal to 0.005% and particularly preferably less than or equal to 0.001% by volume relative to the total volume of fraction A.

Fraction A is characterized by a content of sulfur compounds that is advantageously less than or equal to 0.005%, preferably less than or equal to 0.002% and particularly preferably less than or equal to 0.001% by volume relative to the total volume of fraction A.

Fraction A contains at least 10%, preferably at least 20% and particularly preferably at least 40% of the ethylene contained in the dry gas mixture. Fraction A advantageously contains at most 90%, preferably at most 80% and particularly preferably at most 60% of the ethylene contained in the dry gas mixture.

Advantageously, fraction F1 contains at most 30%, preferably at most 20% and particularly preferably at most 15% of the compounds that are lighter than ethylene contained in the dry gas mixture.

Fraction F1 advantageously contains at least 0.1%, preferably at least 0.3% and particularly preferably at least 0.5% by weight of ethylene relative to the total weight of fraction F1. Fraction F1 preferably contains at most 20%, preferably at most 15% and particularly preferably at most 12% by weight of ethylene relative to the total weight of fraction F1.

Fraction F1 advantageously contains at least 0.3%, preferably at least 0.8% and particularly preferably at least 1% by weight of ethane relative to the total weight of fraction F1. Fraction F1 advantageously contains at most 25%, preferably at most 20%, particularly preferably at most 18% by weight of ethane relative to the total weight of fraction F1.

Fraction F1 is characterized, in addition, by an acetylene content that is advantageously less than or equal to 0.1%, preferably less than or equal to 0.05% and particularly preferably less than or equal to 0.01% by weight relative to the total weight of fraction F1.

Fraction F1 is characterized by a content of compounds comprising at least 3 carbon atoms that is advantageously less than or equal to 1%, preferably less than or equal to 0.5% and particularly preferably less than or equal to 0.1% by weight relative to the total weight of fraction F1.

Fraction F1 is characterized by a content of sulfur compounds that is advantageously less than or equal to 0.005%, preferably less than or equal to 0.002% and particularly preferably less than or equal to 0.001% by weight relative to the total weight of fraction F1.

According to step d) of the process according to the invention, fraction A is conveyed to a chlorination reactor in which most of the ethylene present in fraction A is converted into 1,2-dichloroethane and the 1,2-dichloroethane obtained is optionally separated from the stream of products derived from the chlorination reactor.

The chlorination reaction is advantageously carried out in a liquid phase (preferably mainly DCE) containing a dissolved catalyst such as $FeCl_3$ or another Lewis acid. It is possible to advantageously combine this catalyst with cocatalysts such as alkali metal chlorides. A pair which has given good results is the complex of $FeCl_3$ with LiCl (lithium tetrachloroferrate—as described in Patent Application NL 6901398).

The amounts of $FeCl_3$ advantageously used are around 1 to 30 g of $FeCl_3$ per kg of liquid stock. The molar ratio of $FeCl_3$ to LiCl is advantageously around 0.5 to 2.

In addition, the chlorination process is preferably performed in a chlorinated organic liquid medium. More preferably, this chlorinated organic liquid medium, also called liquid stock, is mainly composed of DCE.

The chlorination process according to the invention is advantageously carried out at temperatures between 30 and 150° C. Good results have been obtained regardless of the pressure both at a temperature below the boiling point (chlorination under subcooled conditions) and at the boiling point itself (chlorination on boiling).

When the chlorination process according to the invention is a chlorination process under subcooled conditions, it gave good results by operating at a temperature which was advantageously greater than or equal to 50° C. and preferably greater than or equal to 60° C., but advantageously less than or equal to 80° C. and preferably less than or equal to 70° C., and with a pressure in the gas phase advantageously greater than or equal to 1 and preferably greater than or equal to 1.1 bar absolute, but advantageously less than or equal to 30, preferably less than or equal to 25 and particularly preferably less than or equal to 20 bar absolute.

A process for chlorination at boiling point is particularly preferred, which makes it possible, where appropriate, to usefully recover the heat of reaction. In this case, the reaction advantageously takes place at a temperature greater than or equal to 60° C., preferably greater than or equal to 70° C. and particularly preferably greater than or equal to 85° C., but advantageously less than or equal to 150° C. and preferably less than or equal to 135° C., and with a pressure in the gas phase advantageously greater than or equal to 0.2, preferably greater than or equal to 0.5, particularly preferably greater than or equal to 1.1 and more particularly preferably greater than or equal to 1.3 bar absolute, but advantageously less than or equal to 20 and preferably less than or equal to 15 bar absolute.

The chlorination process may also be a hybrid loop-cooled process for chlorination at boiling point. The expression "hybrid loop-cooled process for chlorination at boiling point" is understood to mean a process in which cooling of the reaction medium is carried out, for example by means of an exchanger immersed in the reaction medium or by a loop circulating in an exchanger, while producing in the gaseous phase at least the amount of DCE formed. Advantageously, the reaction temperature and pressure are adjusted for the DCE produced to exit in the gas phase and for the remainder of the heat from the reaction medium to be removed by means of the exchange surface.

Fraction A containing the ethylene and also the chlorine (itself pure or diluted) may be introduced, together or separately, into the reaction medium by any known device. A separate introduction of fraction A may be advantageous in order to increase its partial pressure and to facilitate its dissolution which often constitutes a limiting step of the process.

The chlorine is added in a sufficient amount to convert most of the ethylene and without requiring the addition of an excess of unconverted chlorine. The chlorine/ethylene ratio used is preferably between 1.2 and 0.8 and particularly preferably between 1.5 and 0.95 mol/mol.

The chlorinated products obtained mainly contain DCE and also small amounts of by-products such as 1,1,2-trichloroethane or small amounts of ethane or methane chlorination products.

The separation of the DCE obtained from the stream of products derived from the chlorination reactor is optional. In certain cases it may be advantageous not to isolate the DCE formed in the chlorination reactor from the stream of products derived from the chlorination reactor, especially when step e) takes place. Preferably however, the DCE formed in the chlorination reactor is isolated from the stream of products derived from the chlorination reactor.

When it takes place, the separation of the DCE obtained from the stream of products derived from the chlorination reactor is carried out according to known methods and in general makes it possible to exploit the heat of the chlorination reaction. It is then preferably carried out by condensation and gas/liquid separation.

According to the optional step e) of the process according to the invention, the stream of products derived from the chlorination reactor, from which the 1,2-dichloroethane has optionally been extracted, is optionally subjected to an absorption A2 which consists of separating said stream into a fraction enriched with ethane F2 which is then reconveyed to fraction F1 and into a fraction enriched with compounds that are lighter than ethane F2'.

Thus, the stream of products derived from the chlorination reactor, from which the 1,2-dichloroethane has optionally been extracted, is subjected to an absorption step A2 in which said stream is preferably brought into contact with a washing agent containing DCE.

The washing agent that can be used for the absorption step A2 therefore advantageously contains DCE in the liquid state. The presence, in said washing agent, of other compounds is not at all excluded from the scope of the invention. However, it is preferred that the washing agent contain at least 50 vol % of DCE, more particularly at least 80 vol % and most particularly preferably at least 95 vol %.

The washing agent used for the absorption step A2 may be composed of fresh washing agent of any origin, for example crude DCE exiting the chlorination unit, crude DCE exiting the oxychlorination unit or a mixture of the two which has not been purified. It may also be composed of said DCE that has been previously purified or of all or part of fraction F3 recovered during the desorption step D of the process according to the invention optionally containing the DCE formed in the chlorination reactor and extracted in the desorption step, after an optional treatment making it possible to reduce the concentration, in DCE, of the compounds that are heavier than ethane as explained below in the description of step c), optionally with the addition of fresh washing agent.

Preferably, the washing agent used for the absorption step A2 is composed of all or part of fraction F3 recovered during the desorption step D of the process according to the invention optionally containing the DCE formed in the chlorination reactor and extracted in the desorption step, after the above-mentioned optional treatment, optionally with the addition of fresh washing agent. In the case where the DCE formed in the chlorination reaction is isolated from the stream of products derived from the chlorination reaction at the chlorination outlet, in a particularly preferred manner, the washing agent used for the absorption step A2 is composed of all or part of fraction F3 recovered during the desorption step D of the process according to the invention, after the aforementioned optional treatment, with the addition of fresh washing agent (to compensate for losses of washing agent during the absorption and desorption steps).

An essential advantage lies in the fact that the presence of this DCE is not at all troublesome, as it is the compound mainly formed during the oxychlorination or chlorination.

The ratio between the respective throughputs of washing agent and ethane to be extracted from the stream of products derived from the chlorination reactor, from which the 1,2-dichloroethane has optionally been extracted, is not critical and may vary to a large extent. It is in practice limited only by the cost of regenerating the washing agent. In general, the throughput of washing agent is at least one 1, preferably at least 5 and particularly preferably at least 10 tonnes per tonne of the sum of ethane and the compounds that are lighter than ethane contained in the stream of products derived from the chlorination reactor, from which the DCE has optionally been extracted. In general, the throughput of washing agent is at most 100, preferably at most 50 and particularly preferably at most 25 tonnes per tonne of ethane contained in the stream of products derived from the chlorination reactor, from which the 1,2-dichloroethane has optionally been extracted.

The absorption step A2 is advantageously carried out by means of an absorber such as, for example, a falling or rising film absorber or an absorption column chosen from plate columns, columns with random packing, columns with structured packing, columns combining one or more of the aforementioned internals and spray columns. The absorption step A2 is preferably carried out by means of an absorption column and particularly preferably by means of a plate absorption column.

The absorption column is advantageously equipped with associated accessories such as, for example, at least one condenser or chiller that is internal or external to the column.

The aforementioned absorption step A2 is advantageously carried out at a pressure of at least 6, preferably at least 8 and particularly preferably at least 10 bar absolute. The absorption step A2 is advantageously carried out at a pressure of at most 40, preferably at most 35 and particularly preferably at most 30 bar absolute.

The temperature at which the absorption step A2 is carried out is advantageously at least −10, preferably at least 0 and particularly at least 10° C. at the top of the absorber or absorption column. It is advantageously at most 60, preferably at most 50 and particularly preferably at most 40° C. at the top of the absorber or absorption column.

The temperature at the bottom of the absorber or absorption column is at least 0, preferably at least 10 and particularly preferably at least 20° C. It is advantageously at most 70, preferably at most 60 and particularly preferably at most 50° C.

The optional step e) of absorption A2 consists of separating the stream of products derived from the chlorination reactor, from which the 1,2-dichloroethane has optionally been extracted, into a fraction enriched with ethane F2 which is then reconveyed to fraction F1 and into a fraction enriched with compounds that are lighter than ethane F2'.

Fraction F2' is enriched with the compounds that are lighter than ethane. The compounds that are lighter than ethane are generally ethylene, methane, nitrogen, oxygen, hydrogen and carbon monoxide.

Advantageously, fraction F2' contains at least 80%, preferably at least 85% and particularly preferably at least 90% by weight of compounds that are lighter than ethane contained in the stream of products derived from the chlorination reactor subjected to step e).

Advantageously, fraction F2' contains at most 99.99%, preferably at most 99.95% and particularly preferably at most 99.9% by weight of compounds that are lighter than ethane present in the stream of products subjected to step e).

Advantageously, fraction F2' contains at most 20%, preferably at most 12% and particularly preferably at most 8% of the ethane contained in the stream of products subjected to step e).

Advantageously, fraction F2' contains at most 20%, preferably at most 15% and particularly preferably at most 10% of the compounds that are lighter than ethylene contained in the stream of products subjected to step e).

The fraction enriched with ethane F2 advantageously contains at most 0.01%, preferably at most 0.007% and particularly preferably at most 0.005% by weight of hydrogen relative to the total weight of fraction F2.

Fraction F2 advantageously contains at least 0.1%, preferably 0.3% and particularly preferably at least 0.5% by weight of ethane relative to the total weight of fraction F2. Fraction F2 advantageously contains at most 25%, preferably at most 20% and particularly preferably at most 18% by weight of ethane relative to the total weight of fraction F2.

Fraction F2 is characterized, in addition, by an acetylene content that is advantageously less than or equal to 0.1%, preferably less than or equal to 0.05% and particularly preferably less than or equal to 0.01% by weight relative to the total weight of fraction F2.

Fraction F2 is characterized by a content of compounds comprising at least 3 carbon atoms that is advantageously less than or equal to 1%, preferably less than or equal to 0.5% and particularly preferably less than or equal to 0.1% by weight relative to the total weight of fraction F2.

Fraction F2 is characterized by a content of sulfur compounds that is advantageously less than or equal to 0.005%, preferably less than or equal to 0.002% and particularly preferably less than or equal to 0.001% by weight relative to the total weight of fraction F2.

Fraction F2' recovered after step e) is advantageously developed as a fuel. Thus, it may be developed as a fuel in the DCE pyrolysis step or in the ODH step a).

According to step f) of the process according to the invention, fraction F1, optionally containing fraction F2 recovered in step e) of absorption A2, is subjected to a desorption D which consists of separating fraction F1 into a fraction enriched with ethylene (fraction B) and into a fraction F3, optionally containing the DCE formed in the chlorination reactor then extracted, if it has not previously been extracted, which is recycled to at least one of the optional absorption steps after an additional treatment intended to reduce the concentration of the compounds that are heavier than ethane in fraction F3.

The desorption step is advantageously a desorption step in which fraction B is extracted from the washing agent.

The washing agent recovered after the desorption step optionally containing the DCE formed in the chlorination reactor then extracted may be removed, completely or partly conveyed to the oxychlorination sector where the DCE comes together with the DCE formed in the oxychlorination reactor, or completely or partly reconveyed to one of the absorption steps of the process according to the invention, optionally after the previously mentioned treatment (step c)), with the optional addition of fresh washing agent. Preferably, the washing agent recovered after the desorption step is reconveyed to one of the absorption steps of the process according to the invention, after the abovementioned optional treatment, with optional addition of fresh washing agent, or to the oxychlorination sector. In the case where the DCE formed in the chlorination reactor is isolated from the stream of products derived from the chlorination reactor at the chlorination outlet, in a particularly preferred manner, the washing agent recovered after the desorption step is completely or partly reconveyed to one of the absorption steps of the process according to the invention, after the abovementioned optional treatment, with addition of fresh washing agent.

The desorption step is advantageously carried out by means of a desorber such as, for example, a climbing film or falling film desorber, a reboiler or a desorption column chosen from plate columns, columns with random packing, columns with structured packing, columns combining one or more of the aforementioned internals and spray columns. The desorption step is preferably carried out by means of a desorption column and particularly preferably by means of a plate desorption column.

The desorption column is advantageously equipped with associated accessories such as, for example, at least one condenser or one chiller that is internal or external to the column and at least one reboiler.

The desorption step is advantageously carried out at a pressure of at least 1, preferably at least 2 and particularly preferably at least 3 bar absolute. The desorption step is advantageously carried out at a pressure of at most 20, preferably at most 15 and particularly preferably at most 10 bar absolute.

The temperature at which the desorption step is carried out is advantageously chosen so that more than 90%, preferably more than 95% of the ethylene and ethane contained in fraction F1 optionally containing fraction F2 are found in fraction B. The temperature at which the desorption step is carried out is advantageously at least −10, preferably at least 0 and particularly preferably at least 10° C. at the top of the desorber or desorption column. It is advantageously at most 60, preferably at most 50 and particularly preferably at most 40° C. at the top of the desorber or desorption column.

The temperature at the bottom of the desorber or desorption column is at least 60, preferably at least 80 and particularly preferably at least 100° C. It is advantageously at most 200, preferably at most 160 and particularly preferably at most 150° C.

The desorption step f) consists of separating fraction F1, optionally containing fraction F2 recovered in step e) of absorption A2, into a fraction B which is a fraction enriched with ethylene and into a fraction F3 optionally containing the DCE formed in the chlorination reactor then extracted, if it has not previously been extracted, which is recycled to at least one of the absorption steps, optionally after an additional treatment intended to remove the compounds that are heavier than ethane.

Advantageously, fraction B contains at most 1%, preferably at most 0.5% and particularly preferably at most 0.2% by volume of hydrogen relative to the total volume of fraction B.

Fraction B is characterized by an ethylene content that is advantageously greater than or equal to 2%, preferably greater than or equal to 3% and particularly preferably greater than or equal to 4% by volume relative to the total volume of fraction B.

Fraction B is characterized by an ethane content that is advantageously less than or equal to 98%, preferably less than or equal to 97% and particularly preferably less than or equal to 96% by volume relative to the total volume of fraction B.

Fraction B advantageously contains at most 0.01%, preferably at most 0.005% and particularly preferably at most 0.001% of compounds comprising at least 3 carbon atoms relative to the total volume of fraction B.

Fraction B is characterized, in addition, by an acetylene content that is advantageously less than or equal to 0.1%, preferably less than or equal to 0.05% and particularly preferably less than or equal to 0.01% by volume relative to the total volume of fraction B.

Fraction B is characterized by a content of sulfur compounds that is advantageously less than or equal to 0.005%, preferably less than or equal to 0.002% and particularly preferably less than or equal to 0.001% by volume relative to the total volume of fraction B.

Advantageously, fraction F3 contains at least 80%, preferably at least 85% and particularly preferably at least 90% by weight of the compounds that are heavier than ethane contained in fraction F1 optionally containing fraction F2.

Advantageously, fraction F3 contains at most 0.5%, preferably at most 0.3% and particularly preferably at most 0.1% by weight of ethane relative to the total weight of fraction F3.

Advantageously, fraction F3 contains at most 0.3%, preferably at most 0.1% and particularly preferably at most 0.05% by weight of ethylene relative to the total of weight of fraction F3.

According to step g) of the process according to the invention, fraction B is conveyed to an oxychlorination reactor in which most of the ethylene present in fraction B is converted into 1,2-dichloroethane, the 1,2-dichloroethane obtained is separated from the stream of products derived from the oxychlorination reactor and it is optionally added to the DCE formed in the chlorination reactor.

The oxychlorination reaction is advantageously carried out in the presence of a catalyst comprising active elements, including copper, deposited on an inert support. The inert support is advantageously chosen from alumina, silica gels, mixed oxides, clays and other supports of natural origin. Alumina constitutes a preferred inert support.

Catalysts comprising active elements which are advantageously at least 2 in number, one of which is copper, are preferred. Among the active elements other than copper, mention may be made of alkali metals, alkaline-earth metals, rare-earth metals and metals from the group composed of ruthenium, rhodium, palladium, osmium, iridium, platinum and gold. The catalysts containing the following active elements are particularly advantageous: copper/magnesium/potassium, copper/magnesium/sodium, copper/magnesium/lithium, copper/magnesium/caesium, copper/magnesium/sodium/lithium, copper/magnesium/potassium/lithium and copper/magnesium/caesium/lithium, copper/magnesium/sodium/potassium, copper/magnesium/sodium/caesium and copper/magnesium/potassium/caesium. The catalysts described in Patent Applications EP-A 255 156, EP-A 494 474, EP-A-657 212 and EP-A 657 213, incorporated by reference, are most particularly preferred.

The copper content, calculated in metal form, is advantageously between 30 and 90 g/kg, preferably between 40 and 80 g/kg and particularly preferably between 50 and 70 g/kg of the catalyst.

The magnesium content, calculated in metal form, is advantageously between 10 and 30 g/kg, preferably between 12 and 25 g/kg and particularly preferably between 15 and 20 g/kg of the catalyst.

The alkali metal content, calculated in metal form, is advantageously between 0.1 and 30 g/kg, preferably between 0.5 and 20 g/kg and particularly preferably between 1 and 15 g/kg of the catalyst.

The Cu/Mg/alkali metal(s) atomic ratios are advantageously 1/0.1-2/0.05-2, preferably 1/0.2-1.5/0.1-1.5 and particularly preferably 1/0.5-1/0.15-1.

Catalysts having a specific surface area measured according to the BET method with nitrogen advantageously comprised between 25 $m^2/g$ and 300 $m^2/g$, preferably between 50 and 200 $m^2/g$ and particularly preferably between 75 and 175 $m^2/g$, are particularly advantageous.

The catalysts may be used in a fixed bed or in a fluidized bed. This second option is preferred. The oxychlorination process is operated under the range of conditions usually recommended for this reaction. The temperature is advantageously between 150 and 300° C., preferably between 200 and 275° C. and most preferably from 215 to 255° C. The pressure is advantageously greater than atmospheric pressure. Values between 2 and 10 bar absolute have given good results. The range between 4 and 7 bar absolute is preferred. This pressure may usefully be adjusted to attain an optimum residence time in the reactor and to keep a constant rate of passage for various speeds of operation. The usual residence times range from 1 to 60 s and preferably from 10 to 40 s.

The source of oxygen for this oxychlorination may be air, pure oxygen or a mixture thereof, preferably pure oxygen. The latter solution, which allows easy recycling of the unconverted reactants, is preferred.

The reactants may be introduced into the bed by any known device. It is generally advantageous to introduce the oxygen separately from the other reactants for safety reasons. These safety reasons also require keeping the gas mixture leaving the reactor or recycled thereto outside the limits of inflammability at the pressures and temperatures in question. It is preferable to maintain a so-called rich mixture, that is to say containing too little oxygen relative to the fuel to ignite. In this regard, the abundant presence (>2 vol %, preferably >5 vol %) of hydrogen would constitute a disadvantage given the wide inflammability range of this compound.

The hydrogen chloride/oxygen ratio used is advantageously between 3 and 6 mol/mol. The ethylene/hydrogen chloride ratio is advantageously between 0.4 and 0.6 mol/mol.

The chlorinated products obtained mainly contain DCE and also small amounts of by-products such as 1,1,2-trichloroethane.

According to step g) of the process according to the invention, the DCE obtained is separated from the stream of products derived from the oxychlorination reactor and is optionally added to the DCE formed in the chlorination reactor.

The separation of the DCE obtained from the stream of products derived from the oxychlorination reactor is carried out according to known methods. It is preferably carried out first by condensation. The heat of the oxychlorination reactor is generally recovered in the vapour state which may be used for the separations or for any other use.

After exiting from the oxychlorination reactor, the stream of products derived from the reactor, from which the DCE has been extracted, is also advantageously washed to recover the unconverted HCl. This washing operation is advantageously an alkaline washing step. It is preferably followed by a gas/liquid separation step which makes it possible to recover the DCE formed in liquid form and finally to dry the DCE. The gases optionally recycled to the ODH are dried by cooling.

The expression "is optionally added to the DCE formed in the chlorination reactor" is understood to mean that if the DCE formed in the chlorination reactor is isolated from the stream of products derived from this reactor, on exiting the chlorination reactor or after the desorption step D, the DCE formed in the oxychlorination reactor may or may not be added thereto. Preferably, it is added thereto. If on the other hand, this first DCE is not isolated, the DCE isolated from the stream of products derived from the oxychlorination reactor is advantageously the only stream of DCE recovered.

According to optional step h) of the process according to the invention, the stream of products derived from the oxychlorination reactor, from which the DCE has been extracted, optionally containing an additional stream of ethane previously introduced into one of steps b) to g), is optionally recycled to step a) after having been optionally purged of gases and/or after an optional additional treatment in order to eliminate the chlorinated products contained therein.

The stream of products derived from the oxychlorination reactor, from which the DCE has been extracted, may be recycled to step a) or not, during optional step h). Preferably, the stream of products derived from the oxychlorination reactor, from which the DCE has been extracted, is recycled to step a) during step h).

An additional stream of ethane introduced previously into one of steps b) to g) may therefore be found in this stream recycled to step h).

Thus, in the particular case where only a lean ethane stream, for example having 30 or 40 vol % of ethane, is available, it is advantageous to introduce this stream not into step a) directly but, for example, into the absorption/desorption step e') so that the light gases are extracted therefrom and the residual stream is recycled to the ODH during step h).

Similarly, in the particular case where the stream of ethane available is rich in sulfur compounds, it may be advantageous to introduce this stream not into step a) directly but, for example, into step b) to remove these troublesome compounds therefrom; after having undergone steps c) to g), this stream of ethane is then recycled to the ODH during step h).

The stream of products derived from the oxychlorination reactor, from which the DCE has been extracted, is advantageously characterized by an ethane content that is greater than or equal to 10%, preferably greater than or equal to 20%, particularly preferably greater than or equal to 30% and more particularly preferably greater than or equal to 40% by volume relative to the total volume of said stream.

The stream of products derived from the oxychlorination reactor, from which the DCE has been removed, is advantageously characterized by an ethane content that is less than or equal to 90%, preferably less than or equal to 85%, and particularly preferably less than or equal to 80% by volume relative to the total volume of said stream.

The stream of products derived from the oxychlorination reactor, from which the DCE has been extracted, is advantageously characterized by an ethylene content that is less than or equal to 10%, preferably less than or equal to 5% and particularly preferably less than or equal to 2% by volume relative to the total volume of said stream.

The stream of products derived from the oxychlorination reactor, from which the DCE has been extracted, is advantageously characterized by a hydrogen content that is less than or equal to 10%, preferably less than or equal to 5% and particularly preferably less than or equal to 2% by volume relative to the total volume of said stream.

The stream of products derived from the oxychlorination reactor, from which the DCE has been extracted, is advantageously characterized by a carbon monoxide content that is less than or equal to 20%, preferably less than or equal to 15% and particularly preferably less than or equal to 10% by volume relative to the total volume of said stream.

The stream of products derived from the oxychlorination reactor, from which the DCE has been extracted, is advantageously characterized by a carbon dioxide content that is less than or equal to 40%, preferably less than or equal to 35% and particularly preferably less than or equal to 30% by volume relative to the total volume of said stream.

The stream of products derived from the oxychlorination reactor, from which the DCE has been extracted, is advantageously characterized by an oxygen content that is less than or equal to 10%, preferably less than or equal to 5% by volume relative to the total volume of said stream.

According to step h) of the preferred process according to the invention, the stream of products derived from the oxychlorination reactor, from which the DCE has been extracted, optionally containing an additional stream of ethane previously introduced into one of steps b) to g), is recycled to step a).

The recycling to step a) is in this case performed after an optional purge of gases and/or after an optional additional treatment in order to eliminate the chlorinated products (notably traces of DCE and/or of other chlorinated products such as ethylene chloride) contained in the considered stream of products. The additional treatment when it takes place, may be performed by using active carbon or an adsorbent.

Either the purge of gases or the additional treatment or both of them may be performed. More preferably, the stream of products is recycled to step a) without being purged of gases and without any additional treatment in order to eliminate the chlorinated products contained in.

Indeed, the recycling of this stream of products to the ODH step a) may be interesting to benefit from the favourable catalytic effect of the chlorinated products on the ODH reaction.

According to a first preferred mode of the process for the manufacture of DCE starting from a stream of ethane, step e) does not take place.

According to this first preferred mode, the process according to the invention is then characterized in that:
a) the stream of ethane is subjected to a catalytic oxydehydrogenation producing a gas mixture containing ethylene, unconverted ethane, water and secondary constituents;
b) said gas mixture is optionally washed and dried thus producing a dry gas mixture;
c) after an optional additional purification step, said dry gas mixture is subjected to an absorption A1 which consists of separating said gas mixture into a fraction enriched with the compounds that are lighter than ethylene containing some of the ethylene (fraction A) and into a fraction F1;
d) fraction A is conveyed to a chlorination reactor in which most of the ethylene present in fraction A is converted to 1,2-dichloroethane and optionally the 1,2-dichloroethane obtained is separated from the stream of products derived from the chlorination reactor;
f) fraction F1 is subjected to a desorption D which consists of separating fraction F1 into a fraction enriched with ethylene (fraction B) and into a fraction F3 which, after an additional treatment intended to reduce the concentration of the compounds that are heavier than ethane in fraction F3, is recycled to the absorption A1;
g) fraction B is conveyed to an oxychlorination reactor in which most of the ethylene present in fraction B is converted into 1,2-dichloroethane, the 1,2-dichloroethane obtained is separated from the stream of products derived from the oxychlorination reactor and is optionally added to the DCE formed in the chlorination reactor; and
h) the stream of products derived from the oxychlorination reactor, from which the 1,2-dichloroethane has been extracted, is recycled to step a).

According to a second preferred mode of the process for the manufacture of DCE starting from a source of ethane according to the invention, step e) takes place.

According to this second preferred mode, the process according to the invention is then characterized in that:
a) the stream of ethane is subjected to a catalytic oxydehydrogenation producing a gas mixture containing ethylene, unconverted ethane, water and secondary constituents;
b) said gas mixture is optionally washed and dried thus producing a dry gas mixture;
c) after an optional additional purification step, said dry gas mixture is subjected to an absorption A1 which consists of separating said gas mixture into a fraction enriched with the compounds that are lighter than ethylene containing some of the ethylene (fraction A) and into a fraction F1;
d) fraction A is conveyed to a chlorination reactor in which most of the ethylene present in fraction A is converted to 1,2-dichloroethane and the 1,2-dichloroethane obtained is separated from the stream of products derived from the chlorination reactor;
e) the stream of products derived from the chlorination reactor, from which the 1,2-dichloroethane has optionally been extracted, is subjected to an absorption A2 which consists of separating said stream into a fraction enriched with ethane F2 which is then conveyed back to fraction F1, and into a fraction enriched with compounds that are lighter than ethane F2';
f) fraction F1 is subjected to a desorption D which consists of separating fraction F1 into a fraction enriched with ethylene (fraction B) and into a fraction F3 which, after an additional treatment intended to reduce the concentration of the compounds that are heavier than ethane in fraction F3, is recycled to the absorption A1;
g) fraction B is conveyed to an oxychlorination reactor in which most of the ethylene present in fraction B is converted into 1,2-dichloroethane, the 1,2-dichloroethane obtained is separated from the stream of products derived from the oxychlorination reactor and is optionally added to the DCE formed in the chlorination reactor; and
h) the stream of products derived from the oxychlorination reactor, from which the 1,2-dichloroethane has been extracted, is recycled to step a).

The first preferred mode of the process according to the invention is particularly preferred to the second.

The DCE obtained by chlorination and by oxychlorination of ethylene may then be converted into VC.

The invention therefore also relates to a process for the manufacture of VC. To this effect, the invention relates to a process for the manufacture of VC characterized in that:
a) a stream of ethane is subjected to a catalytic oxydehydrogenation producing a gas mixture containing ethylene, unconverted ethane, water and secondary constituents;
b) said gas mixture is optionally washed and dried thus producing a dry gas mixture;
c) after an optional additional purification step, said dry gas mixture is subjected to an absorption A1 which consists of separating said gas mixture into a fraction enriched with the compounds that are lighter than ethylene containing some of the ethylene (fraction A) and into a fraction F1;
d) fraction A is conveyed to a chlorination reactor in which most of the ethylene present in fraction A is converted to 1,2-dichloroethane and optionally the 1,2-dichloroethane obtained is separated from the stream of products derived from the chlorination reactor;
e) optionally the stream of products derived from the chlorination reactor, from which the 1,2-dichloroethane has optionally been extracted, is subjected to an absorption A2 which consists of separating said stream into a fraction enriched with ethane F2 which is then conveyed back to fraction F1, and into a fraction enriched with compounds that are lighter than ethane F2';

f) fraction F1, optionally containing fraction F2 recovered in step e) of absorption A2, is subjected to a desorption D which consists of separating fraction F1 into a fraction enriched with ethylene (fraction B) and into a fraction F3, optionally containing the 1,2-dichloroethane formed in the chlorination reactor then extracted if it has not been extracted previously, which is recycled to at least one of the absorption steps, optionally after an additional treatment intended to reduce the concentration of compounds that are heavier than ethane in fraction F3;

g) fraction B is conveyed to an oxychlorination reactor in which most of the ethylene present in fraction B is converted into 1,2-dichloroethane, the 1,2-dichloroethane obtained is separated from the stream of products derived from the oxychlorination reactor and is optionally added to the 1,2-dichloroethane formed in the chlorination reactor;

h) the stream of products derived from the oxychlorination reactor, from which the 1,2-dichloroethane has been extracted, optionally containing an additional stream of ethane previously introduced in one of steps b) to g), is optionally recycled to step a) after having been optionally purged of gases and/or after an optional additional treatment in order to eliminate the chlorinated products contained therein; and i) the 1,2-dichloroethane obtained is subjected to a pyrolysis thus producing VC.

The particular conditions and preferences defined for the process for the manufacture of DCE according to the invention apply to the process for the manufacture of VC according to the invention.

The conditions under which the pyrolysis may be carried out are known to a person skilled in the art. This pyrolysis is advantageously achieved by a reaction in the gas phase in a tube furnace. The usual pyrolysis temperatures extend between 400 and 600° C. with a preference for the range between 480° C. and 540° C. The residence time is advantageously between 1 and 60 seconds with a preference for the range of 5 to 25 seconds. The conversion rate of the DCE is advantageously limited to 45 to 75% in order to limit the formation of by-products and fouling of the furnace pipes. The following steps make it possible, using any known device, to collect the purified VC and the hydrogen chloride to be upgraded preferably in the oxychlorination. Following purification, the unconverted DCE is advantageously reconveyed to the pyrolysis furnace.

In addition, the invention also relates to a process for the manufacture of PVC. To this effect, the invention relates to a process for the manufacture of PVC characterized in that:

a) a stream of ethane is subjected to a catalytic oxydehydrogenation producing a gas mixture containing ethylene, unconverted ethane, water and secondary constituents;

b) said gas mixture is optionally washed and dried thus producing a dry gas mixture;

c) after an optional additional purification step, said dry gas mixture is subjected to an absorption A1 which consists of separating said gas mixture into a fraction enriched with the compounds that are lighter than ethylene containing some of the ethylene (fraction A) and into a fraction F1;

d) fraction A is conveyed to a chlorination reactor in which most of the ethylene present in fraction A is converted to 1,2-dichloroethane and optionally the 1,2-dichloroethane obtained is separated from the stream of products derived from the chlorination reactor;

e) optionally the stream of products derived from the chlorination reactor, from which the 1,2-dichloroethane has optionally been extracted, is subjected to an absorption A2 which consists of separating said stream into a fraction enriched with ethane F2 which is then conveyed back to fraction F1, and into a fraction enriched with compounds that are lighter than ethane F2';

f) fraction F1, optionally containing fraction F2 recovered in step e) of absorption A2, is subjected to a desorption D which consists of separating fraction F1 into a fraction enriched with ethylene (fraction B) and into a fraction F3, optionally containing the 1,2-dichloroethane formed in the chlorination reactor then extracted if it has not been extracted previously, which is recycled to at least one of the absorption steps, optionally after an additional treatment intended to reduce the concentration of compounds that are heavier than ethane in fraction F3;

g) fraction B is conveyed to an oxychlorination reactor in which most of the ethylene present in fraction B is converted into 1,2-dichloroethane, the 1,2-dichloroethane obtained is separated from the stream of products derived from the oxychlorination reactor and is optionally added to the 1,2-dichloroethane formed in the chlorination reactor;

h) the stream of products derived from the oxychlorination reactor, from which the 1,2-dichloroethane has been extracted, optionally containing an additional stream of ethane previously introduced in one of steps b) to g), is optionally recycled to step a) after having been optionally purged of gases and/or after an optional additional treatment in order to eliminate the chlorinated products contained therein;

i) the 1,2-dichloroethane obtained is subjected to a pyrolysis thus producing VC; and j) the VC is polymerized to produce PVC.

The particular conditions and preferences defined for the process for the manufacture of DCE and the process for the manufacture of VC according to the invention apply to the process for the manufacture of PVC according to the invention.

The process for the manufacture of PVC may be a bulk, solution or aqueous dispersion polymerization process, preferably it is an aqueous dispersion polymerization process.

The expression "aqueous dispersion polymerization" is understood to mean radical polymerization in aqueous suspension and also radical polymerization in aqueous emulsion and polymerization in aqueous microsuspension.

The expression "radical polymerization in aqueous suspension" is understood to mean any radical polymerization process performed in aqueous medium in the presence of dispersants and oil-soluble radical initiators.

The expression "radical polymerization in aqueous emulsion" is understood to mean any radical polymerization process performed in aqueous medium in the presence of emulsifiers and water-soluble radical initiators.

The expression "polymerization in aqueous microsuspension", also called polymerization in homogenized aqueous dispersion, is understood to mean any radical polymerization process in which oil-soluble initiators are used and an emulsion of monomer droplets is prepared by virtue of a powerful mechanical stirring and the presence of emulsifiers.

In relation to a similarly simplified thermal cracking process, the process according to the invention making use of an ODH step has the advantage of combining an endothermic step (ethane converted into ethylene) with an exothermic water production step, of taking place at a moderate temperature and of avoiding having to provide the heat of reaction at a high temperature.

The process according to the invention also has the advantage of making it possible to recycle the stream of products derived from the oxychlorination, from which the DCE has been extracted, to the ODH step, thus ensuring an increased conversion of ethane into ethylene. Furthermore, given the moderate temperature of the ODH relative to thermal cracking, even if this recycled stream contains traces of chlorinated organic products such as DCE, their presence does not cause material behaviour and corrosion problems as occur in the case of thermal cracking above 800° C. The presence of chlorinated products may furthermore be advantageous in so far as it allows an increase of the efficiency of the ODH reaction.

The process according to the invention has the advantage of not generating compounds comprising at least 3 carbon atoms in troublesome amounts, these compounds generally being responsible for a certain inhibition during the pyrolysis of the DCE. This inhibition is due to the formation of derivatives such as 1,2-dichloropropane and monochloropropenes. Their aptitude for forming stable allyl radicals explains their powerful inhibitory effect on the pyrolysis of DCE which is carried out by the radical route. The formation of these by-products containing 3 carbon atoms and heavier by-products furthermore constitutes an unnecessary consumption of reactants in the oxychlorination and in the chlorination, or generates costs for destroying them. Furthermore, these heavy compounds contribute to the soiling of the columns and evaporators.

Since the ODH reaction takes place at a lower temperature than thermal cracking, the process according to the invention is advantageously characterized, in addition, by the fact that the formation of heavy compounds by oligomerization is much lower.

The process according to the invention making use of an ODH step also has the advantage of limiting the conversion by passing to the ODH without having to resort to expensive separations such as those that require an ethylene distillation.

Another advantage of the process according to the invention is that it makes it possible to have, on the same industrial site, a completely integrated process ranging from the hydrocarbon source—namely ethane—up to the polymer obtained starting from the monomer manufactured.

The second variant of the process according to the invention, according to which the ODH takes place at temperatures less than or equal to 650° C., has the advantage of generating very small amounts of hydrogen, responsible for numerous drawbacks.

The first preferred mode of the process according to the invention will now be illustrated with reference to the drawing accompanying the present description. This drawing consists of the appended FIG. 1, schematically representing an embodiment of the process for the manufacture of DCE according to the invention.

A source of ethane 1 and a source of oxygen 2 are introduced into the reactor 3 in order to be subjected to an ODH therein. The gas mixture containing ethylene, unconverted ethane, water and secondary constituent 4 produced during the ODH step is subjected to washing and drying in 5 to remove by-products as well as water (6) therefrom. After an optional additional purification step, the dry gas mixture formed 7 is then conveyed to an absorption column 8 equipped with a condenser. Washing agent from the desorption column 9 is introduced into the absorption column 8 via the line 10, after having been cooled and repressurized respectively in the exchangers 11 and 11' and the pump 12. Fresh washing agent is added via the line 13 to the washing agent from column 9 and a purge 13b is which conveys the washing agent towards an additional treatment (not shown) intended to reduce the concentration of the compounds that are heavier than ethane in the washing agent so that it is then reconveyed to the line 10.

After passing into column 8, the dry gas mixture 7 is separated into the fraction 14 exiting from the top of column 8 and into the fraction 15 exiting from the bottom of column 8. Fraction 14, enriched with the compounds that are lighter than ethylene containing some of the ethylene, is conveyed to a chlorination sector 16 comprising the chlorination reactor supplied with chlorine 17 and the equipment necessary for the separation of the 1,2-dichloroethane formed 18, particularly by condensation and gas/liquid separation, from the stream of products derived from the chlorination reactor and eliminating the residual gases 18b is non converted in the chlorination, among which hydrogen, which may be valorised thermally, chemically or hydraulically.

Fraction 15 comprising DCE enriched with ethylene is then introduced into the desorption column 9 after having been reheated in the exchanger 16'.

After passing into the desorption column 9 equipped with a bottom reboiler and an overhead condenser, fraction 15 is separated into fraction 19 exiting from the top of column 9 and into fraction 20 exiting from the bottom of column 9. Fraction 19, being characterized by a very low hydrogen content, is conveyed to the ethylene oxychlorination unit 21 supplied with oxygen 22 and with hydrogen chloride 23. Fraction 20 mainly containing DCE is reconveyed to the column 8 via the line 10 as explained above. The exchangers 11 and 16' are coupled together with a view to saving energy.

The stream of products 25 derived from the oxychlorination reactor is separated in 21b is in DCE 24 accompanied by liquefied by-products among which water, by condensation followed by washing and gas/liquid separation. The stream of products 26 derived from the oxychlorination reactor from which has been extracted the DCE 24 is then recycled to the reactor 3.

Figure 2:
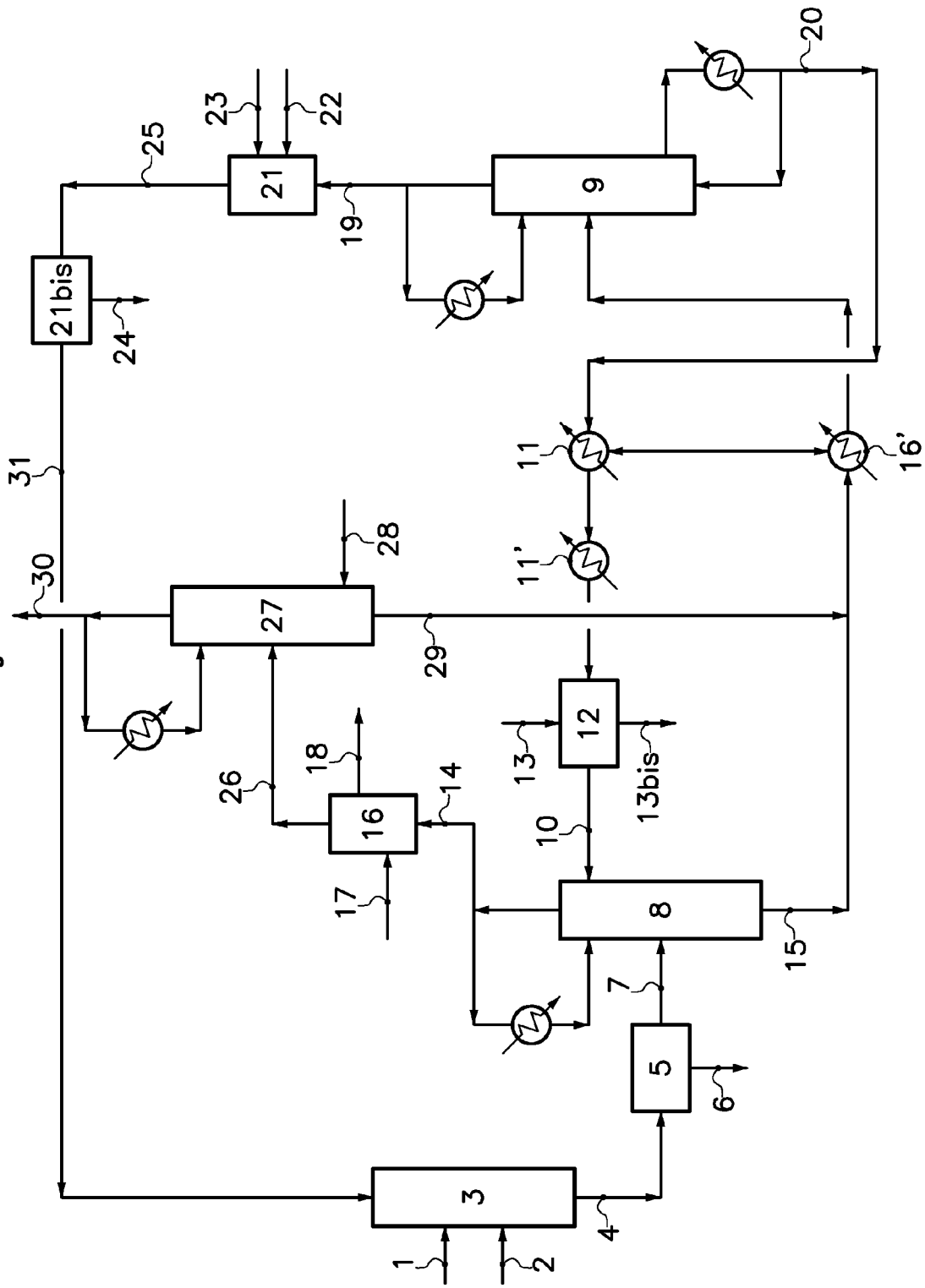
FIG. 2 illustrates a second preferred mode of the process for the manufacture of DCE according to the invention.

The second preferred mode of the process according to the invention will now be illustrated with reference to the drawing accompanying the present description. This drawing consists of the appended FIG. 2, schematically representing an embodiment of the process for the manufacture of DCE according to the invention.

A source of ethane 1 and a source of oxygen 2 are introduced into the reactor 3 in order to be subjected to an ODH therein. The gas mixture containing ethylene, unconverted ethane, water and secondary constituent 4 produced during the ODH step is subjected to washing and drying in 5 in order to remove by-products as well as water (6) therefrom. After an optional additional purification step, the dry gas mixture formed 7 is then conveyed to an absorption column 8 equipped with a condenser. Washing agent from the desorption column 9 is introduced into the absorption column 8 via the line 10, after having been cooled and repressurized respectively in the exchangers 11 and 11' and the pump 12. Fresh washing agent is added via the line 13 to the washing agent from column 9 and a purge 13b is which conveys the washing agent to an additional treatment (not shown) intended to reduce the concentration of the compounds that are heavier than ethane in the washing agent so that it is then reconveyed to the line 10.

After passing into column 8, the dry gas mixture 7 is separated into the fraction 14 exiting from the top of column 8 and into the fraction 15 exiting from the bottom of column 8. Fraction 14, enriched with the compounds that are lighter than ethylene containing some of the ethylene, is conveyed to a chlorination sector 16 comprising the chlorination reactor supplied with chlorine 17 and the equipment necessary for the separation of the 1,2-dichloroethane formed 18, particularly by condensation and gas/liquid separation, from the stream of products derived from the chlorination reactor.

The stream of products 26 derived from the chlorination sector, from which the 1,2-dichloroethane has been extracted, is conveyed into an absorption column 27 equipped with a condenser and supplied with washing agent 28 where it is separated into a fraction enriched with ethane 29 reconveyed to the fraction 15 and into a fraction enriched with compounds that are lighter than ethane 30 which may be valorised thermally, chemically or hydraulically.

Fraction 15 comprising DCE enriched with ethylene is then introduced into the desorption column 9 after having been reheated in the exchanger 16'.

After passing into the desorption column 9 equipped with a bottom reboiler and an overhead condenser, fraction 15 is separated into fraction 19 exiting from the top of column 9 and into fraction 20 exiting from the bottom of column 9. Fraction 19, being characterized by a very low hydrogen content, is conveyed to the ethylene oxychlorination unit 21 supplied with oxygen 22 and with hydrogen chloride 23. Fraction 20 mainly containing DCE is reconveyed to column 8 via the line 10 as explained above. The exchangers 11 and 16' are coupled together with a view to saving energy.

The stream of products 25 derived from the oxychlorination reactor is separated in 21b is in DCE 24 accompanied by liquefied by-products among which water, by condensation followed by washing and gas/liquid separation. The stream of products 31 derived from the oxychlorination reactor from which has been extracted the DCE 24 is then recycled to the reactor 3.

The invention claimed is:

1. A process for the manufacture of 1,2-dichloroethane starting from a stream of ethane, comprising:
    a) subjecting the stream of ethane to a catalytic oxydehydrogenation thus producing a gas mixture containing ethylene, unconverted ethane, water and secondary constituents;
    b) drying said gas mixture thus producing a dry gas mixture, wherein said gas mixture is optionally washed before or after said drying;
    c) after an optional additional purification step, subjecting said dry gas mixture to an absorption A1 which consists of separating said gas mixture into a fraction enriched with the compounds that are lighter than ethylene containing some of the ethylene (fraction A) and into a fraction F1;
    d) conveying said fraction A to a chlorination reactor in which most of the ethylene present in said fraction A is converted to 1,2-dichloroethane, wherein optionally, the 1,2-dichloroethane so obtained is separated from the stream of products derived from the chlorination reactor;
    e) optionally, subjecting the stream of products derived from the chlorination reactor, from which the 1,2-dichloroethane has optionally been extracted, to an absorption A2 which consists of separating said stream into a fraction F2 enriched with ethane which is then conveyed back to said fraction F1, and into a fraction F2' enriched with compounds that are lighter than ethane;
    f) subjecting said fraction F1, optionally containing said fraction F2 recovered in step e) of absorption A2, to a desorption D which consists of separating said fraction F1 into a fraction enriched with ethylene (fraction B) and into a fraction F3, optionally containing the 1,2-dichloroethane formed in the chlorination reactor then extracted if it has not been extracted previously, which is recycled to at least one of the absorption steps, optionally after an additional treatment intended to reduce the concentration of compounds that are heavier than ethane in said fraction F3;
    g) conveying said fraction B to an oxychlorination reactor in which most of the ethylene present in said fraction B is converted into 1,2-dichloroethane, wherein the 1,2-dichloroethane so obtained is separated from the stream of products derived from the oxychlorination reactor and is optionally added to the 1,2-dichloroethane formed in the chlorination reactor; and
    h) optionally, recycling to step a) the stream of products derived from the oxychlorination reactor, from which the 1,2-dichloroethane has been extracted, optionally containing an additional stream of ethane previously introduced in one of steps b) to g), after having been optionally purged of gases and/or after an optional treatment in order to eliminate the chlorinated products contained therein.

2. The process according to claim 1, wherein the source of ethane contains at least 80 vol % of ethane.

3. The process according to claim 1, wherein the source of ethane contains at least 98 vol % of ethane.

4. The process according to claim 1, wherein the catalytic oxydehydrogenation from step a) takes place at a temperature less than or equal to 650° C.

5. The process according to claim 1, wherein during step b), said gas mixture is washed then dried, thus producing a dry gas mixture.

6. The process according to claim 1, wherein during step c) of absorption A1, the dry gas mixture is brought into contact with a washing agent containing 1,2-dichloroethane.

7. The process according to claim 1, wherein said fraction A contains at least 70 wt % of the compounds that are lighter than ethylene contained in the dry gas mixture.

8. The process according to claim 1, wherein said fraction B is characterized by an ethylene content greater than or equal to 2 vol % relative to the volume of said fraction B.

9. The process according to claim 1, wherein step e) does not take place.

10. A process for manufacturing vinyl chloride, comprising:
    a) subjecting a stream of ethane to a catalytic oxydehydrogenation thus producing a gas mixture containing ethylene, unconverted ethane, water and secondary constituents;
    b) drying said gas mixture thus producing a dry gas mixture, wherein said gas mixture is optionally washed before or after said drying;
    c) after an optional additional purification step, subjecting said dry gas mixture to an absorption A1 which consists of separating said gas mixture into a fraction enriched with the compounds that are lighter than ethylene containing some of the ethylene (fraction A) and into a fraction F1;
    d) conveying said fraction A to a chlorination reactor in which most of the ethylene present in said fraction A is converted to 1,2-dichloroethane, wherein optionally, the 1,2-dichloroethane so obtained is separated from the stream of products derived from the chlorination reactor;
    e) optionally, subjecting the stream of products derived from the chlorination reactor, from which the 1,2-dichloroethane has optionally been extracted, to an absorption A2 which consists of separating said stream into a fraction F2 enriched with ethane which is then conveyed back to said fraction F1, and into a fraction F2' enriched with compounds that are lighter than ethane;

f) subjecting said fraction F1, optionally containing said fraction F2 recovered in step e) of absorption A2, to a desorption D which consists of separating said fraction F1 into a fraction enriched with ethylene (fraction B) and into a fraction F3, optionally containing the 1,2-dichloroethane formed in the chlorination reactor then extracted if it has not been extracted previously, which is recycled to at least one of the absorption steps, optionally after an additional treatment intended to reduce the concentration of compounds that are heavier than ethane in said fraction F3;

g) conveying said fraction B to an oxychlorination reactor in which most of the ethylene present in said fraction B is converted into 1,2-dichloroethane, wherein the 1,2-dichloroethane so obtained is separated from the stream of products derived from the oxychlorination reactor and is optionally added to the 1,2-dichloroethane formed in the chlorination reactor;

h) optionally, recycling to step a) the stream of products derived from the oxychlorination reactor, from which the 1,2-dichloroethane has been extracted, optionally containing an additional stream of ethane previously introduced in one of steps b) to g), after having been optionally purged of gases and/or after an optional treatment in order to eliminate the chlorinated products contained therein; and i) subjecting the 1,2-dichloroethane so obtained to a pyrolysis thus producing vinyl chloride.

11. A process for manufacturing polyvinyl chloride, comprising:

a) subjecting a stream of ethane to a catalytic oxydehydrogenation thus producing a gas mixture containing ethylene, unconverted ethane, water and secondary constituents;

b) drying said gas mixture thus producing a dry gas mixture, wherein said gas mixture is optionally washed before or after said drying;

c) after an optional additional purification step, subjecting said dry gas mixture to an absorption A1 which consists of separating said gas mixture into a fraction enriched with the compounds that are lighter than ethylene containing some of the ethylene (fraction A) and into a fraction F1;

d) conveying said fraction A to a chlorination reactor in which most of the ethylene present in said fraction A is converted to 1,2-dichloroethane, wherein optionally, the 1,2-dichloroethane obtained is separated from the stream of products derived from the chlorination reactor;

e) optionally, subjecting the stream of products derived from the chlorination reactor, from which the 1,2-dichloroethane has optionally been extracted, to an absorption A2 which consists of separating said stream into a fraction F2 enriched with ethane which is then conveyed back to said fraction F1, and into a fraction F2' enriched with compounds that are lighter than ethane;

f) subjecting said fraction F1, optionally containing said fraction F2 recovered in step e) of absorption A2, to a desorption D which consists of separating said fraction F1 into a fraction enriched with ethylene (fraction B) and into a fraction F3, optionally containing the 1,2-dichloroethane formed in the chlorination reactor then extracted if it has not been extracted previously, which is recycled to at least one of the absorption steps, optionally after an additional treatment intended to reduce the concentration of compounds that are heavier than ethane in said fraction F3;

g) conveying said fraction B to an oxychlorination reactor in which most of the ethylene present in said fraction B is converted into 1,2-dichloroethane, wherein the 1,2-dichloroethane so obtained is separated from the stream of products derived from the oxychlorination reactor and is optionally added to the 1,2-dichloroethane formed in the chlorination reactor;

h) optionally, recycling to step a) the stream of products derived from the oxychlorination reactor, from which the 1,2-dichloroethane has been extracted, optionally containing an additional stream of ethane previously introduced in one of steps b) to g), after having been optionally purged of gases and/or after an optional treatment in order to eliminate the chlorinated products contained therein;

i) subjecting the 1,2-dichloroethane so obtained to a pyrolysis thus producing vinyl chloride; and j) polymerizing the vinyl chloride to produce polyvinyl chloride.

12. The process according to claim 1, wherein mixed oxides containing both Mo and V; W and V or Mo; or W and V are used as a catalytic system to carry out the catalytic oxydehydrogenation.

13. The process according to claim 12, wherein the mixed oxides are selected from the group consisting of Mo—W—V—Ta—Te—Ti—P—Ni—Ce—O, Mo—W—V—Ta—Te—Ti—P—O, Mo—W—V—Te—Ti—P—Ce—O, Mo—W—V—Te—Ti—P—Ni—O, Mo—W—V—Te—Ti—P—O, Mo—W—V—Te—Ti—O, Mo—W—V—Te—P—O, Mo—W—V—Te—O, Mo—W—V—Ta—Te—Ti—P—Ni—Ce—O, Mo—W—V—Ta—Te—Ti—P—O, Mo—W—V—Te—Ti—P—Ce—O, Mo—W—V—Te—Ti—P—Ni—O, Mo—W—V—Te—Ti—P—O, Mo—W—V—Te—Ti—O, Mo—W—V—Te—P—O, Mo—W—V—Te—O, Mo—W—V—Nb—O, Mo—W—V—Sb—O, Mo—W—V—Ti—Sb—Bi—O, Mo—W—V—Ti—Sb—O, Mo—W—V—Sb—Bi—O, Mo—W—V—Zr—O, Mo—W—V—Nb—Ta—O, Mo—W—V—Nb—O, and Mo—W—V—O.

14. The process according to claim 10, wherein during step c) of absorption A1, the dry gas mixture is brought into contact with a washing agent containing 1,2-dichloroethane.

15. The process according to claim 10, wherein said fraction A contains at least 70 wt % of the compounds that are lighter than ethylene contained in the dry gas mixture.

16. The process according to claim 10, wherein said fraction B is characterized by an ethylene content greater than or equal to 2 vol % relative to the volume of said fraction B.

17. The process according to claim 10, wherein step e) does not take place.

18. The process according to claim 10, wherein mixed oxides containing both Mo and V; W and V or Mo; or W and V are used as a catalytic system to carry out the catalytic oxydehydrogenation.

19. The process according to claim 18, wherein the mixed oxides are selected from the group consisting of Mo—W—V—Ta—Te—Ti—P—Ni—Ce—O, Mo—W—V—Ta—Te—Ti—P—O, Mo—W—V—Te—Ti—P—Ce—O, Mo—W—V—Te—Ti—P—Ni—O, Mo—W—V—Te—Ti—P—O, Mo—W—V—Te—Ti—O, Mo—W—V—Te—O, Mo—W—V—Ta—Te—Ti—P—Ni—Ce—O, Mo—W—V—Ta—Te—Ti—P—O, Mo—W—V—Te—Ti—P—Ce—O, Mo—W—V—Te—Ti—P—Ni—O, Mo—W—V—Te—Ti—P—O, Mo—W—V—Te—Ti—O, Mo—W—V—Te—P—O, Mo—W—V—Te—O, Mo—W—V—Nb—O, Mo—W—V—Sb—O, Mo—W—V—Ti—Sb—Bi—O, Mo—W—V—Ti—Sb—O, Mo—W—V—Sb—Bi—O, Mo—W—V—Zr—O, Mo—W—V—Nb—Ta—O, Mo—W—V—Nb—O, and Mo—W—V—O.

20. The process according to claim 11, wherein during step c) of absorption A1, the dry gas mixture is brought into contact with a washing agent containing 1,2-dichloroethane.

21. The process according to claim 11, wherein said fraction A contains at least 70 wt % of the compounds that are lighter than ethylene contained in the dry gas mixture.

22. The process according to claim 11, wherein said fraction B is characterized by an ethylene content greater than or equal to 2 vol % relative to the volume of said fraction B.

23. The process according to claim 11, wherein step e) does not take place.

24. The process according to claim 11, wherein mixed oxides containing both Mo and V; W and V or Mo; or W and V are used as a catalytic system to carry out the catalytic oxydehydrogenation.

25. The process according to claim 24, wherein the mixed oxides are selected from the group consisting of Mo—W—V—Ta—Te—Ti—P—Ni—Ce—O, Mo—W—V—Ta—Te—Ti—P—O, Mo—W—V—Te—Ti—P—Ce—O, Mo—W—V—Te—Ti—P—Ni—O, Mo—W—V—Te—Ti—P—O, Mo—W—V—Te—Ti—O, Mo—W—V—Te—P—O, Mo—W—V—Te—O, Mo—W—V—Ta—Te—Ti—P—Ni—Ce—O, Mo—W—V—Ta—Te—Ti—P—O, Mo—W—V—Te—Ti—P—Ce—O, Mo—W—V—Te—Ti—P—Ni—O, Mo—W—V—Te—Ti—P—O, Mo—W—V—Te—Ti—O, Mo—W—V—Te—P—O, Mo—W—V—Te—O, Mo—W—V—Nb—O, Mo—W—V—Sb—O, Mo—W—V—Ti—Sb—Bi—O, Mo—W—V—Ti—Sb—O, Mo—W—V—Sb—Bi—O, Mo—W—V—Zr—O, Mo—W—V—Nb—Ta—O, Mo—W—V—Nb—O, and Mo—W—V—O.

* * * * *